(12) United States Patent
Nuijens

(10) Patent No.: US 7,544,853 B2
(45) Date of Patent: *Jun. 9, 2009

(54) C1 INHIBITOR WITH SHORT HALF-LIFE TRANSIENT TREATMENT

(75) Inventor: Johannes Henricus Nuijens, Amsterdam (NL)

(73) Assignee: Pharming Intellectual Property B.V., Al Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 10/557,026

(22) PCT Filed: May 14, 2004

(86) PCT No.: PCT/NL2004/000330

§ 371 (c)(1),
(2), (4) Date: Feb. 21, 2007

(87) PCT Pub. No.: WO2004/100982

PCT Pub. Date: Nov. 25, 2004

(65) Prior Publication Data

US 2007/0185011 A1  Aug. 9, 2007

(51) Int. Cl.
C12P 21/00 (2006.01)
A61K 38/00 (2006.01)
(52) U.S. Cl. ............................................ 800/7; 514/12
(58) Field of Classification Search ........................ None
See application file for complete search history.

(56) References Cited

U.S. PATENT DOCUMENTS 7,067,713 B2 * 6/2006 Nuijens et al. ................ 800/14
2005/0223416 A1 * 10/2005 Nuijens et al. ................. 800/7

FOREIGN PATENT DOCUMENTS

| EP | 0586909 A2 | 3/1994 |
|---|---|---|
| FR | 2601034 A1 | 1/1988 |
| WO | WO 91/06650 A1 | 5/1991 |
| WO | WO 92/22320 A1 | 12/1992 |
| WO | WO 96/03051 A1 | 2/1996 |
| WO | WO 01/57079 A2 | 8/2001 |

OTHER PUBLICATIONS

Bos et al. Expression of Recombinant C1-Inhibitor in the Methylotrophic. 2002, International Immunopharm., vol. 2, No. 9, pp. 1330, abs. 11.*

Akita, N., et al., "The effect of C 1 esterase inhibitor on ischemia: reperfusion injury in the rat brain," *No To Shinkei*, vol. 53(7), pp. 641-644 (2001) [Article in Japanese] *English Abstract only*.

Bork, et al., "Long-Term Prophylaxis with C1-inhibitor (C1 INH) Concentrate in Patients with Recurrent Angioedema Caused by Hereditary and Acquired C1-Inhibitor Deficiency," *J. Allergy Clinical Immunology*, vol. 83, pp. 677-682 (1989).

Bos, I.G.A., et al., "Recombinant human C1-inhibitor produced in *Pichia pastoris* has the same inhibitory capacity as plasma C1-inhibitor," *Biochimica et Biophysica Acta*, vol. 1648, pp. 75-83 (2003).

Carter P. et al., *Euro J. Biochem*. 173;163, (1988).

Chu, L. and D.K. Robinson, "Industrial choices for protein production by large-scale cell culture," *Current Opinion in Biotechnology*, vol. 12, pp. 180-187 (2001).

Cicardi, M. et al., *Immunobiol*. 199:366, (1998).

Davis A.E., *Ann. Rev. Immunol.* 6:595-628 (1988).

De Filippi, F et al., *Transfusion* 38:307, (1998).

Eldering, E. et al., "Expression of functional human C1 inhibitor in COS cells," *J. Biol. Chem.* vol. 263(24), pp. 11776-11779 (1988).

Gonçalves, M.A.F.V, "A concise peer into the background, initial thoughts and practices in human gene therapy," *Bioessays*, vol. 27, pp. 506-517 (2005).

Hack, C. et al., *LANCET*, 339:8789 378, (1992).

Houdebine, L.M., "Transgenic Animal Bioreactor," *Transgenic Res.*, vol. 9 (4-5), pp. 305-320 (2000).

Koles, K., et al., "Influence of Lactation Parameters on the N-Glycosylation of Recombinant Human C1 Inhibitor Isolated from the Milk of Transgenic Rabbits," *Glycobiology*, vol. 14(11), pp. 979-986 (2004).

Lamark, T., et al., "Expression of active human C1 inhibitor in serpin domain of *Escherichia coli*," *Protein Expression and Purification*, vol. 22, pp. 349-358 (2001).

Marasini, B., et al., "Treatment of hereditary angioedema," *Klin Wochenschr.*, vol. 56(16), pp. 819-823 (1978) [Article in German] *English Abstract only*.

Rai, M. and H. Padh, "Expression of systems for production of heterologous proteins," *Current Science*, vol. 80(9,10), pp. 1121-1128 (2001).

Schapira, M. et al., *Complement* 2:111 (1985).

Shoenberger. O.L., "Characterization of carbohydrate chains of C1-inhibitor and desialylated C1-inhibitor," *FEBS*, vol. 314, pp. 430-434 (1992).

(Continued)

*Primary Examiner*—Deborah Crouch
(74) *Attorney, Agent, or Firm*—Townsend and Townsend and Crew LLP

(57) ABSTRACT

The present invention relates to the use of a C1 inhibitor (C1INH) with shorter half-life than plasma-derived C1INH for the preparation of a medicament for the transient treatment of an individual. It relates to both therapeutic and prophylactic treatment. The method of the invention allows for the administration of C1INH at certain therapeutic levels for a concise pre-determined time span. Pharmaceutical compositions based on C1INH with shorter half-lives may be used both in situations where transient treatment is merely and advantage. The advantage of the use according to the invention is that an individual is not exposed to C1INH for longer than required, since the levels of the C1INH more rapidly subsides after administration has stopped. In contrast, levels of plasma-derived C1INH would remain elevated for a prolonged period of time.

14 Claims, 3 Drawing Sheets

OTHER PUBLICATIONS

Wolff, M.W., et al., "Expression of C1 esterase inhibitor by the baculovirus expression vector system: Preparation, purification and characterization," *Protein Expression and Purification*, vol. 22, pp. 414-421 (2001).

Wurm, F.M., "Production of recombinant protein therapeutics in cultivated mammalian cells," *Nature Biotechnology*, vol. 22(11), pp. 1393-1398 (2004).

Zurlo J. et al. *Fertility and Sterility* 54:64, (1990).

* cited by examiner

_US 7,544,853 B2_

C1 INHIBITOR WITH SHORT HALF-LIFE TRANSIENT TREATMENT

FIELD OF THE INVENTION

The present invention relates to the controlled delivery of a pharmaceutical composition. In particular, it relates to the controlled delivery of a pharmaceutical composition which comprises a glycoprotein.

BACKGROUND OF THE INVENTION

It is well recognised that in therapy one is always looking for a balance between the curing effect of a pharmaceutically active compound and the detrimental side effects the active compound may exert. From this point of view, it is of prime concern not to use more of an active compound then necessary and not to use it for a longer period than required. At the same time, there is the challenge of the effective delivery of a pharmaceutically active compound to an active site and of achieving an acceptable rate of release of the pharmaceutically active compound. These issues have our constant attention in developing and improving pharmaceutical therapies.

Many approaches have been adopted to attempt to deal with these issues. For example, a particularly high dose of a pharmaceutically active compound may be administered to ensure that at least an effective amount of it reaches the desired site of treatment. This approach to administration is clearly problematic, because at high dose the pharmaceutically active compound may exerts its detrimental effects. For example, see Horstick et al (2001) Circulation 104:3125. They describe how C1INH significantly protects ischemic tissue from reperfusion damage at 40 IU/kg, but provokes detrimental effects at overly high doses (a dose of 100 IU/kg or more).

There remains a need for methods for delivering a pharmaceutically active compound with maximum effectiveness. This method should allow for the administration of a patient's dose requirement of optimal effectivity, while minimising undesirable side effects.

LEGENDS TO THE FIGURES

FIG. 1. shows the time profiles of mean functional C1INH (U/mL) in the distinct dosage groups. The SD in the highest dosage group (100 U/kg) is presented by a bar.

DETAILED DESCRIPTION

Figure 1:
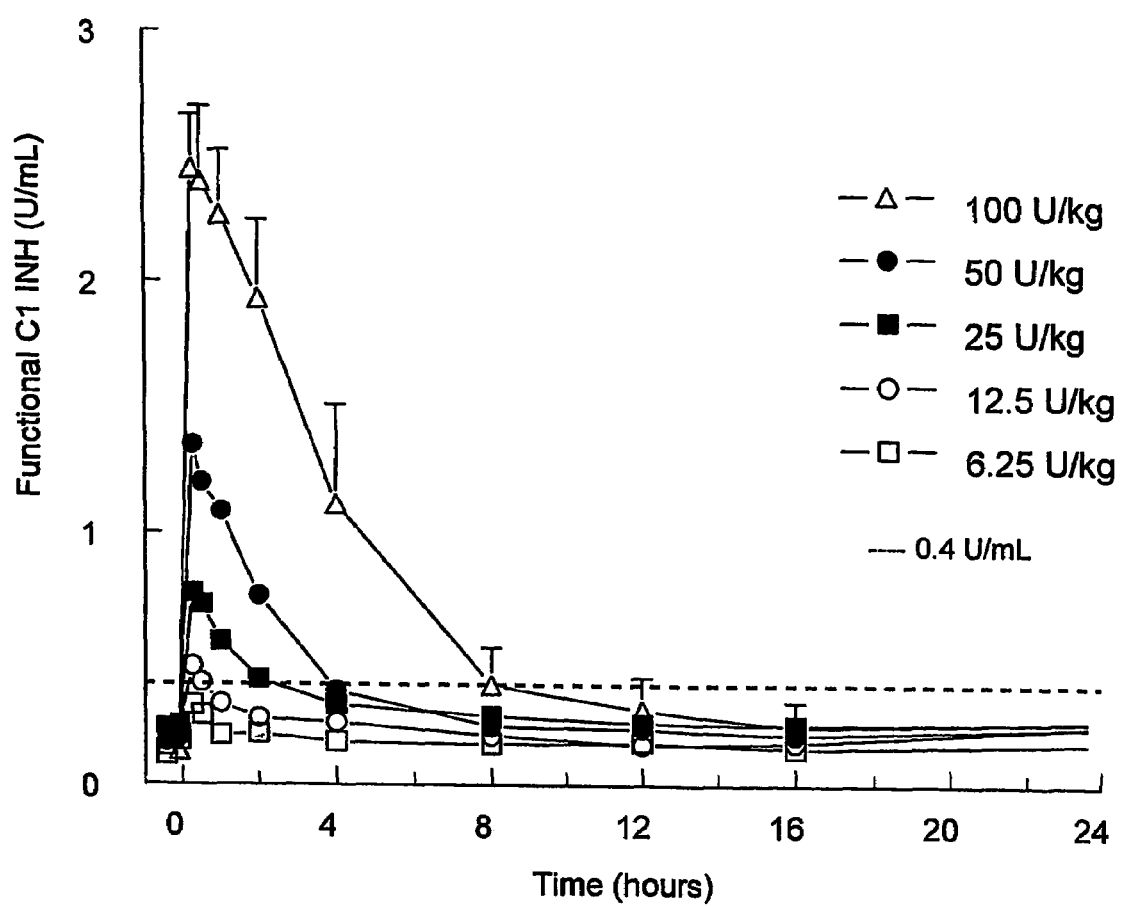
Figure 2:
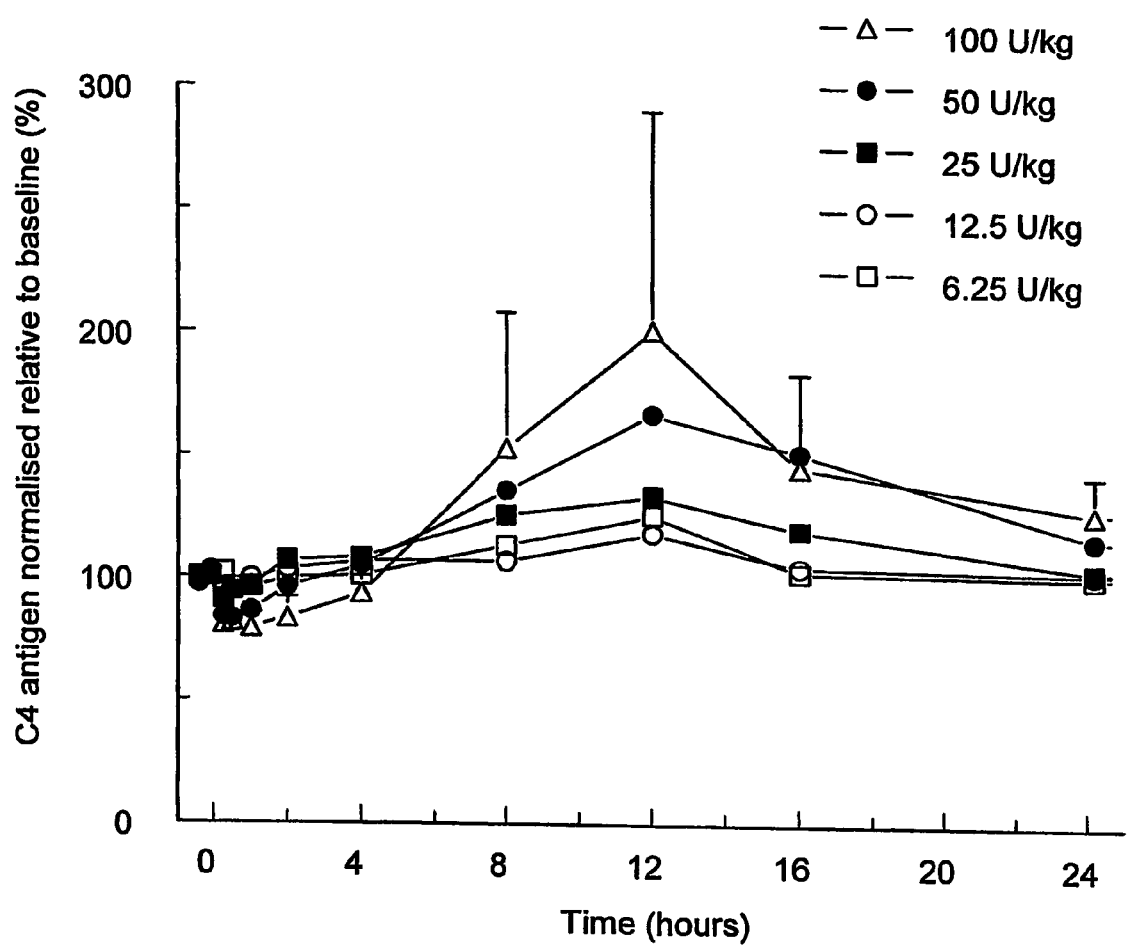
FIG. 2 shows the time profiles of mean normalised C4 antigen (%) in the distinct dosage groups. The SD in the highest dosage group (100 U/kg) is presented by a bar.

The present invention relates to the use of a C1 inhibitor (C1INH) with shorter half-life than its naturally occurring counterpart for the preparation of a medicament for the transient treatment of an individual.

In this context, "naturally occurring counterpart" refers to naturally occurring C1INH which is typically derived from plasma.

In this context, "treatment" refers to treatment of individuals who are already with the disorder as well as those susceptible to the disorder or those in which the disorder is to be prevented. In other words, it relates to both therapeutic and prophylactic treatment. In this context, "transient treatment" refers to the administration of C1INH at certain therapeutic levels for a concise pre-determined time-span. In this context, "individual" refers to any individual, both human and non-human, both young and old, both ill and asymptomatic.

In this context, half-life refers to the amount of time after which half of the total amount of C1INH brought in circulation has been cleared from the blood stream. The protein sequence of a C1INH with shorter half-life is typically the same or substantially the same, i.e. more than 70%, preferably more than 80, 85, 90 or 95% the same as the protein sequence of plasma-derived C1INH. It may have been obtained from plasma derived C1INH after modification, but also by independent production.

The advantage of the use according to the invention is that an individual is not exposed to C1INH for longer than required, since the levels of C1INH more rapidly subside after administration has stopped. In contrast, levels of plasma-derived C1INH would remain elevated for a prolonged period of time. This may be unnecessary or be associated to certain health risks. In particular for the treatment of acute cases, where a high initial dosis is required or advantageous for successful treatment, the use of C1INH with a shorter half-life may result in a better ratio of beneficial effects and adverse reactions. This high initial dose may be at least 1,5, at least 2, 3 or 4 times the dosis of the natural occurring counterpart which would be administered. The use of proteins with a shorter half-life allows for the exposure of an individual to an active compound at a certain level for a concise predetermined time span.

Transient Treatment

Transient treatment may be essential or highly desired if the individual who receives the treatment is already weak or infirm. Such may be the case if the individual is of high age or very young, e.g. a new born or is weakened, e.g. due to a condition or disease, or even due to other treatments.

Transient treatment may also be essential if the pharmaceutical agent which is used for treatment is very strong and demanding on the receiving individual. Unnecessary long exposure of an individual to such pharmaceutical agents should be prevented as much as possible. To this end, the C1INH with shorter half-life may, for instance, be coupled to a cytostatic agent or to an isotope which should be removed from circulation as soon as possible after its has had its effect, to avoid detrimental side-effects caused by this cytotoxic compound as much as possible.

Transient treatment also allows for the treatment of a condition or disease which requires precise control of the dosage of the medicament, such as when working with pharmaceutical agents which posses a very narrow range of therapeutic effectiveness. For example, some drugs require a large amount to be injected in the blood stream to ensure that an adequate dose and concentration will be delivered to the affected area. As long as the drugs are in the blood stream, they may cause side effects on other organs in the body, particularly if they remain present after the therapeutic effect has been achieved. The use of the present invention reduces the risks of side effects, since the drug with the shorter half-life is more rapidly cleared from the body than its counterpart with the longer half-life. This means that the drug is cleared after it has exerted its beneficial effects and its presence is not considered necessary anymore.

Transient treatment may also be used in acute cases where a high initial dose is required or advantageous for successful treatments.

Production of the Protein with a Shorter Half-Life

A C1INH with shorter half-life, be it a naturally occurring or a recombinantly produced C1INH, may be prepared by any convenient method. It may for example be prepared by in vivo or in vitro modification of its carbohydrate structure. Modifications to the carbohydrate structure include modifications which lead to underglycosylation, overglycosylation, to the asialio form of C1INH, or any other modifications which lead to a different glycosylation pattern.

In vitro, underglycosylation may be the result of a deletion of a carbohydrate moiety or of a complete carbohydrate chain of C1INH. Modifications may involve both N- or O-linked carbohydrate chains, or only one type of chain. It may involve all the chains, or only some of the chains. Overglycosylation may for instance be the result of the addition of an extra carbohydrate moiety or a complete carbohydrate chain to the C1INH molecule. An asialo-form of C1INH may typically be obtained by removal of a sialic acid group. It is well-known that the half-life of a glycoprotein in the blood is highly dependent on the composition and structure of its N- and O-linked carbohydrate groups. In general, maximal half-life of a glycoprotein requires that its N- and O-linked carbohydrate groups have a terminal sialic acid. If this terminal sialic acid is not present, the glycoprotein is rapidly cleared from the blood due to the exposure of galactose residues. It is well-established that the presence of terminal galactose residues in carbohydrate moieties of glycoproteins results in enhanced plasma clearance by the asialoglycoprotein receptor in the liver. Sialic acid may be removed in several ways. For instance, it may be removed chemically or enzymatically, for example, by treatment with sialidase.

In vivo, modifications of carbohydrate chains of C1INH may be introduced by using recombinant production systems. Both prokaryotic and eukaryotic cell cultures may be used, such as yeast cells, fungal cells, insect cells and mammalian cells. For example, COS cells and CHO cells are suitable mammalian production systems. Although mammalian cell culture systems have the capacity to produce glycoproteins with sialylated carbohydrate groups, optimal, natural or complete glycosylation is often difficult to achieve and consequently, recombinantly produced glycoproteins in general have a different glycosylation pattern than their natural counterparts. Such glycoproteins may also be prepared in transgenic animals, preferably in non-human animals, such as in transgenic rabbits, bovine, mice, rats, goats and sheep. The skilled person will understand that it will depend on the specific glycoprotein to be produced and on the amount which has to be produced, which transgenic animal is best used for production.

Different types of modifications to the structure of the carbohydrate chain of the protein, such as different glycosylation, underglycosylation or overglycosylation may be introduced separately or in combination, simultaneously or consecutively, some types may be introduced to one part of the molecule, while others are introduced to another part of the molecule. Preferred combinations of modifications contribute to the shortening of the half-life of the protein by exposing the galactose, N-acetylgalactosamine, mannose, fucose or phosphomannose moieties of the protein.

In a preferred embodiment the C1INH with a shorter half-life has a half-life which is less than 60 or 50%, preferably less than 40, 30, 25 or 20% of the half-life of its naturally occurring counterpart Pharmaceutical Compositions Pharmaceutical compositions based on C1INH with shorter half-life may be used both in situations where transient treatment is a pre-requisite, as well as in situations in which transient treatment is merely an advantage. This is for example the case when using a pharmaceutical composition which does not cause severe toxic side effects, but which side effects are still unpleasant for the individual who is treated. C1INH with a shorter half-life which is used for transient treatment may be part of or combined with state of the art pharmaceutical compositions. These pharmaceutical compositions typically comprise the C1INH with a shorter half-life in association with a carrier or excipient and, optionally, a pharmaceutically acceptable adjuvant.

These pharmaceutical compositions may be administered in a number of ways depending on whether local or systemic treatment is desired, the area to be treated and the stability of the active compound. Suitable formulations will depend on the method of administration. The pharmaceutical composition is preferably administered by parenteral administration, such as for example by intravenous, intra-arterial, subcutaneous, intraperitoneal or intramuscular injection or infusion; or by intrathecal or intracranial administration. In a preferred embodiment it is administered by intravenous infusion. Suitable formulations for parenteral administration are known in the art and are typically liquid formulations. These liquid formulations may for example be administered by an infusion pump.

The effective dose, i.e. effective concentration and frequency, will depend on the specific pharmaceutical composition which is used, the severity of the condition and the general state of the patient's health. In general, the effective dose of a pharmaceutical composition which is based on a C1INH with a shorter half-life may be found by routine optimisation. A suitable starting point is the dose which is used for the equivalent pharmaceutical composition which is based on plasma-derived C1INH. A great advantage of a pharmaceutical composition of the invention is that a high initial dosis may be used in treatment, which enhances the likelihood of successful treatment. This high initial dose is possible because the C1INH in the pharmaceutical composition of the invention shows a faster clearance than its natural counterpart.

A C1INH with shorter half-life may be used to treat any type of disease in which normally a plasma-derived C1INH is used.

For example, underglycosylated C1 esterase INH (C1INH) may be used to replace human plasma derived C1INH. C1INH may be used for the treatment of individuals suffering from any condition or disease associated with an absolute or relative deficiency of functional C1INH. Such deficiency may result in an insufficient control of C1INH on local or systemic activation of inflammatory systems involved in the pathophysiology of said conditions, including the complement and contact systems. Such disorders include: Acquired angioedema (AAE) and hereditary angioedema (HAE), for which conditions acute treatment and short-term prophylaxis can be applied; Sepsis; septic shock, acute respiratory distress syndrome (ARDS), multiple organ failure (MOF) and preeclampsia, vascular leakage syndrome (VLS), graft versus host disease (GVHD), severe burns and thermal trauma; rheumatoid arthritis; systemic lupus erythematosus; meningitis: cardiopulmonary bypass (CPB), extra corporal circulation (ECC), and (hyper)acute graft rejection.

C1INH may also be used for the treatment of individuals suffering from any disorder associated with ischemic reperfusion injury, including: acute myocardial infarction (AMI); ischemic reperfusion injury after emergency coronary surgery for failed percutaneous transluminal coronary angioplasty (PCTA), or after any vascular surgery with blood vessel cross clamping (e.g. of aorta, leading to skeletal muscle ischemia); stroke; after hemorragic shock; after or during ECC; after/during CPB; after/during any transplantation surgery (lung, liver, kidney, heart); intestinal ischemia; pancreatitis after manipulation of pancreatic or bile duct (ERCP).

In one embodiment recombinant human C1INH produced in rabbits is used instead of C1INH from human plasma. The rabbit-derived human C1INH contains about 5-6 fold less sialic acid as compared to its natural counterpart and about 15% of its N-linked glycans are neutral carrying terminal mannose residues, whereas plasma derived C1INH has no oligomannose type glycosylation. The rabbit recombinant human C1INH may be used in higher amounts than plasma derived C1INH without serious adverse side effects, while still having a beneficial effect. In a preferred embodiment, underglycosylated human C1INH is administered intravenously at a dose of more than 25, 50 or 70 U/kg body weight of the individual, preferably more than 80, 100, 150 or 200 U/kg body weight of the individual. One unit (U) of C1INH is the amount of C1INH present in 1 milliliter of human blood. One such unit corresponds to approximately 275 microgram plasma derived C1INH. Assuming a molecular weight of 110,000 dalton, the concentration in human plasma of C1INH is 2.5 micromol per liter (Nuijens et al. (1989), J. Clin. Invest. 84:443).

EXAMPLES

Example 1

Administration of Recombinant Human C1INH

Twelve asymptomatic patients with HAE, with a plasma level of functional C1INH of less than 40% of normal, were included into an open label study. Patients screening occurred at approximately 30 and/or 14 days before the first study drug infusion. The patients were divided into 4 groups (A-D) of 3 patients each and each patient was infused intravenously with recombinant C1INH which was produced in and isolated from the milk of transgenic rabbits as described in WO 01/57079. Patients were infused on two occasions with an interval of at least five weeks between the consecutive drug administrations. The patients stayed at the study centre for 24 hours on both infusion dates. Each patient received the doses (expressed in U/kg) as mentioned in Table 1 below, through a 15 min intravenous infusion. Continuation of dosing and dose escalation was decided after each dose had been given to a group of 3 patients. If a dose was considered safe (by the evaluation of clinical and laboratory safety parameters excluding immunogenicity analysis), the next dose was given to the next group of 3 patients. After the first study period of a subject was completed, all available data were analysed on a per subject basis with emphasis on safety and tolerability, including the immunogenicity analysis at day 22. Provided that no safety concerns including those with regard to immunosafety had arisen in a subject in relation to the first dosing (Study Period 1), and that the subject still met the criteria for eligibility during the second screening period, it was decided to proceed to Study Period 2 with the second exposure to recombinant C1INH at an escalated dosage (see Table 1). All the 12 patients did complete the entire study.

TABLE 1

Phase I Administration schedule of rhC1INH (Units/kg)

| | Study period (occasion) 1 | Washout | Study period (occasion) 2 |
|---|---|---|---|
| Group A | 6.25 | | 25.0 |
| Group B | 12.5 | | 50.0 |
| Group C | 25.0 | | 100 |
| Group D | | 50.0 | 100 |

No probably drug-related adverse events, or changes in ECG, vital signs or routine laboratory parameters were observed. No clinically significant increases in anti-C1INH or anti-HRI were observed. The product did not elicit allergic reactions and none of the patients showed evidence of neutralising antibodies. Thus, rhC1INH appeared safe and well tolerated also in dosis of up to 100 U/kg. Recombinant C1INH administration did not raise concerns relating to immunosafety.

Example 2

Half-Life of Recombinant Human C1INH Isolated from the Milk of Transgenic Rabbits The profiles of functional C1INH (FIG. 1) indicated a full initial recovery and a dose-dependent clearance of rhC1INH, which indicates a saturable mechanism of elimination. This was confirmed by analysing the rate of clearance, half-lifes and endogenous infusion rate, which is shown in Table 2. These were dependent on the dose. Application of the standard model after the infusion of rhC1INH at 100 U/kg revealed a clearance of about 13 mL/min, a half-life of about 3 h, a volume of distribution of about 3 L, and an endogenous infusion rate of about 2 U/min.

TABLE 2

Summary of model-dependent pharmacokinetic parameters (empirical Bayes estimates) of functional C1INH.
Initial model without Michaelis-Menten elimination
Summary table kinetic parameters functional C1 inhibitor; initial model

| Parameter | Treatment | N | Mean | SD | Min | Median | Max |
|---|---|---|---|---|---|---|---|
| Clearance (mL/min) | 6.25 U/kg | 3 | 71.38 | 10.187 | 61.3 | 71.08 | 81.7 |
| | 12.5 U/kg | 3 | 59.54 | 11.820 | 52.1 | 53.36 | 73.2 |

TABLE 2-continued

Summary of model-dependent pharmacokinetic parameters
(empirical Bayes estimates) of functional C1INH.
Initial model without Michaelis-Menten elimination
Summary table kinetic parameters functional C1 inhibitor; initial model

| Parameter | Treatment | N | Mean | SD | Min | Median | Max |
|---|---|---|---|---|---|---|---|
| | 25 U/kg | 6 | 33.92 | 9.664 | 25.7 | 32.40 | 51.9 |
| | 50 U/kg | 6 | 22.78 | 7.344 | 15.7 | 20.76 | 34.0 |
| | 100 U/kg | 6 | 12.65 | 2.505 | 10.6 | 11.36 | 16.3 |
| Half life (min) | 6.25 U/kg | 3 | 28.0 | 13.39 | 13 | 30.8 | 40 |
| | 12.5 U/kg | 3 | 40.1 | 13.69 | 25 | 44.1 | 51 |
| | 25 U/kg | 6 | 73.1 | 13.68 | 55 | 72.8 | 90 |
| | 50 U/kg | 6 | 93.7 | 8.45 | 84 | 93.5 | 104 |
| | 100 U/kg | 6 | 172.1 | 36.10 | 118 | 169.8 | 219 |
| Volume (L) | 6.25 U/kg | 3 | 2.75 | 1.032 | 1.6 | 3.16 | 3.5 |
| | 12.5 U/kg | 3 | 3.29 | 0.624 | 2.6 | 3.39 | 3.9 |
| | 25 U/kg | 6 | 3.50 | 0.845 | 2.5 | 3.26 | 4.7 |
| | 50 U/kg | 6 | 3.03 | 0.794 | 2.2 | 2.98 | 4.1 |
| | 100 U/kg | 6 | 3.10 | 0.720 | 2.4 | 2.96 | 4.3 |
| Endogenous infusion rate (U/min) | 6.25 U/kg | 3 | 12.98 | 5.327 | 9.7 | 10.08 | 19.1 |
| | 12.5 U/kg | 3 | 12.17 | 3.989 | 7.6 | 13.73 | 15.2 |
| | 25 U/kg | 6 | 7.81 | 3.150 | 4.3 | 7.70 | 11.5 |
| | 50 U/kg | 6 | 4.84 | 3.109 | 1.6 | 4.54 | 9.1 |
| | 100 U/kg | 6 | 2.20 | 0.764 | 1.3 | 2.24 | 3.3 |
| Endogenous concentration (U/mL) | 6.25 U/kg | 3 | 0.178 | 0.0501 | 0.14 | 0.164 | 0.23 |
| | 12.5 U/kg | 3 | 0.217 | 0.0983 | 0.10 | 0.264 | 0.28 |
| | 25 U/kg | 6 | 0.239 | 0.0951 | 0.10 | 0.251 | 0.34 |
| | 50 U/kg | 6 | 0.203 | 0.1075 | 0.10 | 0.177 | 0.34 |
| | 100 U/kg | 6 | 0.183 | 0.0804 | 0.09 | 0.173 | 0.29 |

Example 3

Biological Activity of Recombinant Human C1INH

Baseline C4 levels and C4 responses were highly variable between subjects of the distinct dosage groups, which underlines the need to express individual C4 responses relative to individual C4 antigen values at baseline (normalised C4 antigen). Expression of C4 antigen normalised to baseline facilitates the comparison of C4 responses both within and between dosage groups. Thus, the mean of individual baseline C4 levels is arbitrarily set at 100% and changes of C4 levels post-infusion are expressed as percentage change from baseline.

Figure 3:
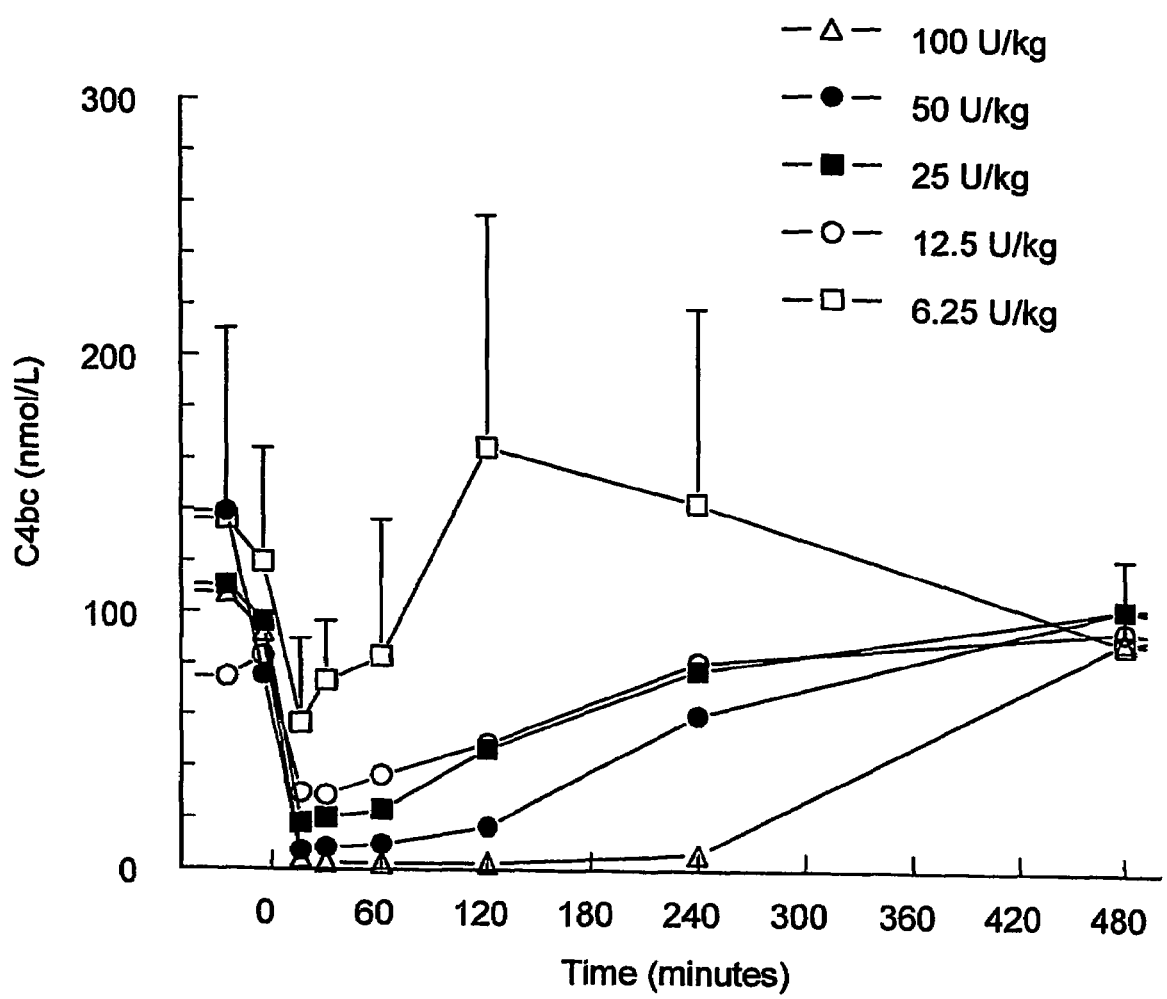
FIG. 3 shows the time profiles of mean C4b/c (nmol/mL) in the distinct dosage groups during the first 8 hours post-infusion. The SD in the lowest dosage group (6.25 U/kg) is presented by a bar.

The increases in functional C1INH resulted in an initial dose-dependent decrease in mean normalised C4 (decrease of about 25% within one hour after 100 U/kg), which was followed by a dose-dependent increase in mean normalised C4 (about 200% after 100 U/kg) which response was highly variable within dosage groups. C4 peak levels occurred at about 12 hours post-infusion and thereafter gradually declined to baseline. An immediate dose-dependent effect of functional C1INH on plasma C4b/c was observed. FIG. 3 shows that the magnitude of the decrease in C4b/c as well as its duration appeared dependent on the dose of functional C1INH.

Combining the profiles of functional C1INH and C4b/c revealed an inverse relationship between functional C1INH and C4b/c. The results indicated that cleavage of C4 starts to occur once functional C1INH drops below a level of about 70% of normal.

The combined effects of functional C1INH on C4 and C4bc indicate that recombinant human C1INH displays biological activity in subjects with HAE.

The invention claimed is:

1. A method of treating an individual suffering from an absolute or relative deficiency of functional C1 inhibitor, comprising
    determining a transient treatment regime of a C1 inhibitor based on it having a shorter half-life than plasma-derived C1 inhibitor;
    administering the C1 inhibitor to the individual in the transient treatment regime.

2. The method according to claim 1 wherein the treatment is for a condition or disease in which it is beneficial to control the concentration or the time span of presence of the C1 inhibitor.

3. The method according to claim 1 wherein the C1 inhibitor with shorter half-life is prepared by modification of the carbohydrate structure of the plasma-derived C1 inhibitor.

4. The method according to claim 3 wherein the half-life of the C1 inhibitor is shortened by the presence of more terminal galactose, N-acetylglucosamine, mannose, fucose or phosphomannose moieties than on the plasma-derived C1 inhibitor.

5. The method according to claim 4 wherein the presence of more terminal galactose, N-acetylglucosamine, mannose, fucose or phosphomannose moieties is due to in vivo or in vitro glycosylation.

6. The method according to claim 1 wherein the C1 inhibitor with shorter half-life is a recombinantly produced C1 inhibitor.

7. The method according to claim 1 wherein the C1 inhibitor with shorter half-life is produced in a microorganism or in a non-human transgenic mammal.

8. The method according to claim 1 wherein the individual is a new-born.

9. The method according to claim 1 wherein the treatment is for an individual suffering from a disorder associated with ischemic reperfusion injury.

10. The method according to claim 1 wherein the individual is suffering from or susceptible to any of acquired angioedema (AAE), hereditary angioedema (HAE), sepsis, septic shock, acute respiratory distress syndrome (ARDS), multiple organ failure (MOF), preeclampsia, vascular leakage syndrome (VLS), graft versus host disease (GVHD), severe burns, thermal trauma; rheumatoid arthritis; systemic lupus erythematosus; meningitis: cardio-pulmonary bypass (CPB), extra corporal circulation (ECC) and (hyper)acute graft rejection; acute myocardial infarction (AMI); ischemic reperfusion injury after emergency coronary surgery for failed percutaneous transluminal coronary angioplasty (PCTA), or after any vascular surgery with blood vessel cross clamping (e.g. of aorta, leading to skeletal muscle ischemia); stroke; after hemorragic shock; after or during ECC; after/during CPB; after/during any transplantation surgery (lung, liver, kidney, heart); intestinal ischemia; pancreatitis after manipulation of pancreatic or bile duct (ERCP).

11. The method according to claim 1 wherein the C1 inhibitor is for intravenous administration at a dose of more than 25 U/kg body weight of the individual.

12. The method according to claim 11 wherein the C1 inhibitor is for intravenous administration at a dose of more than 50 U/kg body weight of the individual.

13. The method according to claim 1 wherein the C1 inhibitor with a shorter half-life has a half-life which is less than 60% of the half-life of plasma-derived C1 inhibitor.

14. The method of claim 1 wherein the dose is higher than that of an equivalent pharmaceutical composition comprising plasma derived C1 inhibitor and clearance is faster relative to that of the plasma-derived C1 inhibitor.

* * * * *